(12) United States Patent
Maleedy

(10) Patent No.: US 11,497,688 B2
(45) Date of Patent: Nov. 15, 2022

(54) TOILETRY PRODUCTS

(71) Applicant: BUBBLE LABORATORIES LIMITED, London (GB)

(72) Inventor: Anthony Maleedy, London (GB)

(73) Assignee: BUBBLE LABORATORIES LIMITED, London (GB)

( * ) Notice: Subject to any disclaimer, the term of this patent is extended or adjusted under 35 U.S.C. 154(b) by 330 days.

(21) Appl. No.: 16/320,744

(22) PCT Filed: Jul. 7, 2017

(86) PCT No.: PCT/GB2017/052000
§ 371 (c)(1),
(2) Date: Jan. 25, 2019

(87) PCT Pub. No.: WO2018/020211
PCT Pub. Date: Feb. 1, 2018

(65) Prior Publication Data
US 2019/0159975 A1    May 30, 2019

(30) Foreign Application Priority Data

Jul. 25, 2016 (GB) .................................. 1612820

(51) Int. Cl.
| | | |
|---|---|---|
| *A61K 8/00* | (2006.01) | |
| *A61K 8/04* | (2006.01) | |
| *A61K 8/42* | (2006.01) | |
| *A61K 8/44* | (2006.01) | |
| *A61K 8/46* | (2006.01) | |
| *A61K 8/60* | (2006.01) | |
| *A61K 8/65* | (2006.01) | |
| *A61Q 19/10* | (2006.01) | |

(52) U.S. Cl.
CPC ............... *A61K 8/042* (2013.01); *A61K 8/42* (2013.01); *A61K 8/44* (2013.01); *A61K 8/466* (2013.01); *A61K 8/602* (2013.01); *A61K 8/65* (2013.01); *A61Q 19/10* (2013.01); *A61K 2800/87* (2013.01)

(58) Field of Classification Search
CPC ...................................................... A61K 8/042
See application file for complete search history.

(56) References Cited

U.S. PATENT DOCUMENTS

| | | | |
|---|---|---|---|
| 3,689,437 A | 9/1972 | Mclaughlin | |
| 7,381,692 B2 * | 6/2008 | Grissett ................ | A61K 8/0208 510/141 |
| 2003/0114520 A1 | 6/2003 | Pereira et al. | |
| 2005/0069514 A1 | 3/2005 | Maleedy | |
| 2007/0110700 A1 * | 5/2007 | Wells ..................... | A61K 8/416 424/70.21 |
| 2012/0101135 A1 | 4/2012 | Klug et al. | |
| 2013/0225472 A1 * | 8/2013 | Wu ........................ | A61K 8/345 510/447 |

FOREIGN PATENT DOCUMENTS

| | | |
|---|---|---|
| EP | 0345885 A2 | 12/1989 |
| GB | 1551587 A | 8/1979 |
| WO | 03066018 A1 | 8/2003 |

OTHER PUBLICATIONS

International Preliminary Report on Patentability issued in PCT/GB2016/053011, dated May 8, 2018, 6 pages.
International Search Report and Written Opinion issued in PCT/GB2016/053011, dated Dec. 12, 2016, 10 pages.
International Search Report and Written Opinion issued in PCT/GB2017/052000, dated Sep. 22, 2017, 13 pages.

* cited by examiner

*Primary Examiner* — Necholus Ogden, Jr.
(74) *Attorney, Agent, or Firm* — Sheridan Ross P.C.

(57) ABSTRACT

The present invention relates to toiletry products and more particularly to shower products that are manufactured in shaped forms and/or comprise shaped gels. Certain embodiments relate to formulations for shower products comprising gelatin, water and surfactant wherein the shower product is in shaped gel form and/or comprises a shaped gel form. Other embodiments relate to shower products per se for example in shaped gel form and/or comprising shaped gel form. Further embodiments relate to a process for the manufacture of such formulations and shower products.

12 Claims, No Drawings

TOILETRY PRODUCTS

CROSS-REFERENCE TO RELATED APPLICATIONS

This application is a U.S. National Stage Application of International Patent Application No. PCT/GB2017/052000, filed Jul. 7, 2017, which claims the benefit of Great Britain Patent Application No. 1612820.9, filed Jul. 25, 2016, the disclosures each of which is expressly incorporated by reference in its entirety.

FIELD OF THE INVENTION

The present invention relates to toiletry products and more particularly to toiletry products that are manufactured in shaped forms. In particular, the invention relates to a shower product, more particularly to a shower product in shaped form, for example in shaped gel form. Certain embodiments of the present invention relate to formulations of shower products which may be manufactured into and/or comprise shaped gel forms. Other embodiments relate to shower products per se for example in shaped gel form. Further embodiments relate to a process for the manufacture of such formulations and shower products in shaped gel form.

BACKGROUND TO THE INVENTION

In the field of personal care and toiletry products, shower products come in many forms such as shower creams, exfoliates, body shampoos, mousses etc. but are almost always in the form of liquid gels, i.e. shower gels, that are dispensed from a container as required and applied to the body by hand or via a cleaning implement, for example a cloth, sponge, loofah etc., to generate a lather on the body.

Liquid shower gels often contain one or more surfactants and a lather is generated when the liquid shower gel is applied to a surface, such as the surface of a body, with agitation, in the presence of water. It is the surfactant that generates the lather and it is known that the degree of lather increases as the amount of surfactant in the product is increased. The amount and quality of the lather generated also depends on the type of surfactant used. However, many surfactants are known to have a drying effect on the skin which can lead to skin irritation and, in some cases, dermatitis. As shower gels are applied directly to the body it is important to use as little surfactant as possible to minimise the risk of dryness and/or irritation to the skin caused by the surfactant. There is thus a balance between safety and functionality that determines the amount of surfactant that can be used in a shower gel. Too much surfactant might result in a good lather but skin dryness and/or irritation for the user whilst too little surfactant may be safer for the user's skin but may result in a poor lather and poor cleaning performance.

Market research has shown that shower products dominated the shower and bath product market in 2014 with a market share of approximately 70% and that liquid shower gels accounted for a large proportion of this percentage. Shower gels are thus very popular toiletry products. However, there are disadvantages associated with liquid shower gels. As liquid gels, they must be kept in a container and the container can only be disposed of when all of the shower gel has been used. There is also a risk of spillage or leakage from the container.

Soap can also be used as a shower product to generate a lather on the body and is often in the form of a solid product, for example a bar of soap. Once removed from the initial packaging, this packaging can be disposed of and the solid soap kept in the vicinity of the shower without packaging and without risk of spillage or leakage. However because soap has a rigid solid structure, it is hard to the touch and does not conform to the contours of the body when in contact with the body which is disadvantageous with regard to cleaning performance and user comfort.

The inventors have therefore identified the need for a shower product which combines the advantages of a liquid shower gel with the solid form of a soap and which can be used like a solid soap. It would be advantageous if a shower product could be developed that combined the advantageous of a liquid shower gel with the solid form of a soap, for example for use like a solid soap.

Bubble bath products in shaped gel forms are known. For example WO 03/066018 discloses a shaped bath gel comprising gelatin and surfactant which rapidly dissipates in a quantity of warm water to create an abundance of foam. However, such products cannot be used as shower products. Firstly, bubble bath products often contain high levels of surfactant which are not safe for direct skin contact and consequently such products should not be applied directly to the body. Secondly, such products are suitable for a single use only as they rapidly dissipate in warm water to release their surfactant load. The shaped gel form does not maintain its structural integrity over an extended use period and/or for multiple uses with controlled and gradual surfactant release.

The inventors have thus identified the need for and provide herein a shower product in a shaped gel form. The shower product of the invention can also be described as having a semi-solid gel form. The invention provides a formulation for and a shower product in shaped gel form that is sufficiently solid to maintain its structural integrity over an extended period of use and/or that can be used multiple times whilst being sufficiently pliant to conform to the contours of the body on application.

Surprisingly, it has been found that a formulation for a shower product comprising gelatin, water and surfactant yields a shower product in a shaped gel form. No such products are believed to exist in the prior art.

Whilst not wishing to be bound by theoretical considerations, it is believed that by selecting gelatin with an appropriate gel structure, it is possible to obtain a shaped gel product that has a degree of structural integrity that is maintained over an extended use period for example for multiple uses, whilst being sufficiently pliant to conform to the contours of the body on application and which releases surfactant in a safe, controlled and gradual manner to produce a lather.

An important characteristic of shower products in shaped gel forms, is that they melt or dissolve in use in a controlled and gradual manner when in contact with water to release surfactant in a quantity to provide the desired lather for the user. The melt characteristics and surfactant release profile of such products are thus critical to the ability of the product to be used as a shower product.

As well as the balance between structural integrity (for prolonged and/or multiple uses) and pliability (for cleaning performance and user comfort), the inventors have also considered the type of surfactant and surfactant release profile (for safety) as well as addition product performance requirements that must be considered in order to provide a commercially viable product.

For example, the product must melt in a steady and consistent way to produce a good quality lather at an appropriate water temperature. For example, it is important that the lather comprises bubbles of the correct size and quantity for cleaning performance and as well as a favourable user experience.

It is also important that such products have a pleasing appearance and tactility. The appearance and tacitility of the produce should be maintainable for an appropriate period of time once it has been removed from its packaging. In this regard it is useful if the product retains moisture content and does not 'dry-out' when exposed to air so as to prevent or minimise product distortion or shrivelling. It is also advantageous if such products have an appropriate shelf life i.e. that they remain effective, useful and suitable for use for a specific period of time.

Safety is a very important consideration. As discussed above, it is important to determine the appropriate quantity of surfactant in a shower product that provides a lather sufficient for a good cleaning performance whilst not having a harmful effect on the skin of the user. In this regard, it would be advantageous if a surfactant known to be mild to skin could be incorporated into a shower product of the invention so that it can be incorporated in a quantity sufficient to provide a plentiful and good quality lather in use. Such considerations are particular important for products intended for use by children or users with sensitive skin or skin conditions.

These various different performance requirements can and do give rise to conflict in terms of arriving at a product formulation which is satisfactory. Fortunately, a shower formulation and product in shaped gel form is disclosed herein which satisfies one or more of these product performance requirements.

It is an aim of aspects of the present invention to at least partially mitigate the problems associated with the prior art and/or as discussed above.

It is an aim of certain embodiments of the present invention to provide a formulation for a shower product in shaped gel form.

It is an aim of certain embodiments of the present invention to provide a shower product in shaped gel form and/or which comprises a shaped gel.

It is an aim of certain embodiments of the present invention to provide a formulation for use in a shower product in shaped gel form which product has a pleasing appearance and tactility.

It is an aim of certain embodiments of the present invention to provide a shower product in or comprising a shaped gel form having a pleasing appearance and tactility.

It is an aim of certain embodiments of the present invention to provide a formulation for use in a shower product in shaped gel form which product retains moisture content when exposed to air.

It is an aim of certain embodiments of the present invention to provide a shower product in shaped gel form which product retains moisture content when exposed to air.

It is an aim of certain embodiments of the present invention to provide a formulation for use in a shower product in shaped gel form which product has an appropriate shelf life.

It is an aim of certain embodiments of the present invention to provide a shower product in shaped gel form having an appropriate shelf life.

It is an aim of certain embodiments of the present invention to provide a formulation for a shower product in shaped gel form which product provides a lather for good cleaning performance and/or for a favourable user experience.

It is an aim of certain embodiments of the present invention to provide a shower product in shaped gel form that provides a lather for good cleaning performance and/or for a favourable user experience.

EMBODIMENTS OF THE INVENTION

In one aspect, the invention provides a formulation for a shower product wherein;
   the formulation comprises gelatin, water and surfactant; and
   the shower product comprises a shaped gel.

Aptly, the shower product is in a shaped gel form. Such shaped gel forms include for example irregularly shaped forms. In certain embodiments, a shower product comprises a shaped gel and may comprise a further component, for example to form a coated and/or encapsulated shaped gel product as described herein. The dimensions of the shaped gel product may be dictated by the dimensions and characteristics of the further component. Further details are provided herein.

In one aspect, the invention provides a shower product in shaped gel form comprising gelatin, water and surfactant.

In one aspect, the invention provides a formulation for a shower product wherein;
   the formulation comprises gelatin, water and surfactant wherein;
      the gelatin has a bloom strength of 170 g to 230 g and is present in a quantity of 5 to 10% by weight; and
      the water is present in a quantity of at least 15% by weight; and
   the shower product is in shaped gel form.

In one aspect, the invention provides a formulation for a shower product wherein;
   the formulation comprises gelatin, water and surfactant wherein;
      the gelatin has a bloom strength of 170 g to 230 g and is present in a quantity of 5 to 10% by weight; and
      the water is present in a quantity of at least 15% by weight; and
   the shower product comprises the formulation in a shaped gel form.

In one aspect, the invention provides a shower product in shaped gel form comprising gelatin, water and surfactant wherein;
   the gelatin has a bloom strength of 170 g to 230 g and is present in a quantity of 5 to 10% by weight; and
   the water is present in a quantity of at least 15% by weight.

In one aspect, the present invention provides a process for the preparation of a formulation for a shower product of the invention comprising the steps of:
   i) mixing gelatin with water;
   ii) adding surfactant to the gelatin mixture and optionally heating, for example to approximately 70° C.;
   iii) optionally, adding any other ingredients to the gelatin mixture;
   iv) if required, adjusting the pH of the gelatin mixture to between pH 5 to pH 7; and optionally,
   v) forming the solution/mixture into the desired shape(s); and/or
   vi) forming a gel, for example by cooling the mixture.

Aptly, the gelatin is dissolved in water in a quantity of from 5 to 10% by weight based on the total weight of the formulation. Aptly, the gelatin has a bloom strength of 170 g to 230 g.

In one aspect, the present invention provides a process for the preparation of a shower product of the invention comprising the steps of:
i) mixing gelatin with water;
ii) adding surfactant to the gelatin mixture and optionally heating, for example to approximately 70° C.;
iii) optionally, adding any other ingredients to the gelatin mixture;
iv) if required, adjusting the pH of the gelatin mixture to between pH 5 to pH 7;
v) forming the mixture into the desired shape(s); and/or
vi) forming a gel, for example by cooling the mixture.

Aptly, the gelatin is dissolved in water in a quantity of from 5 to 10% by weight based on the total weight of the formulation. Aptly, the gelatin has a bloom strength of 170 g to 230 g.

In certain embodiments, step v) comprises pouring the mixture into and/or onto a substrate. In certain embodiments, the substrate is a holed substrate e.g. a mesh. In certain embodiments, the substrate is a porous substrate e.g. a sponge.

In one aspect of the present invention, there is provided a process for the preparation of a shower product of the invention, the process comprising the steps of:
i) mixing gelatin with at least one ingredient to form a gelatin mixture;
ii) adding at least one further ingredient and optionally any other ingredients to the mixture, and optionally heating, for example to approximately 70° C.;
iii) if required, adjusting the pH of the gelatin mixture to between pH 5 to pH 7;
iv) forming the mixture into the desired shape(s); and/or
v) forming a gel, for example by cooling the mixture.

In one aspect of the present invention, there is provided a process for the preparation of a formulation of the invention, the process comprising the steps of:
i) mixing gelatin with at least one ingredient to form a gelatin mixture;
ii) adding at least one further ingredient and optionally any other ingredients to the mixture, and optionally heating, for example to approximately 70° C.;
iii) if required, adjusting the pH of the gelatin mixture to between pH 5 to pH 7;
iv) forming the mixture into the desired shape(s); and/or
v) forming a gel, for example by cooling the mixture.

Aptly, the gelatin has a bloom strength of 170 g to 230 g. In certain embodiments, the process comprises, subsequent to step (ii) and prior to step (iv), a step of agitating the mixture with a mechanical stirrer e.g. for about 10 minutes.

In certain embodiments, the gelatin mixture is cooled subsequently to step (ii) and then re-heated e.g. to about 50° C.

In certain embodiments, step (i) comprises mixing gelatin with one or more of surfactant, water and humectant.

In certain embodiments, step (i) comprises mixing gelatin with a surfactant solution. Aptly, the surfactant solution with which the gelatin is mixed comprises a quantity of surfactant in range of 10 to 40% by weight, for example 20 to 40% by weight, for example 25 to 35% by weight, for example approximately 30% by weight.

Aptly, the surfactant solution with which the gelatin is mixed comprises a quantity of water in range of 90 to 60% by weight, for example 80 to 60% by weight, for example 75 to 65% by weight, for example approximately 70% by weight.

In certain embodiments, step iv) comprises pouring the mixture into and/or onto a substrate. In certain embodiments, the substrate is a holed substrate e.g. a mesh. In certain embodiments, the substrate is a porous substrate e.g. a sponge.

In one aspect, the present invention provides a formulation obtainable by the process described herein. In one aspect the present invention provides a shower product in shaped gel form obtainable by the process described herein.

Gelatin is an important component of the invention. It is gelatin that allows the product to take on a gel form which is thermo-reversible and to be formed into shaped shower products. Gelatin is a protein and, in common with all proteins, is made up of amino acids joined together by peptide linkages to from polymer chains. It is these polymer chains that give gelatin gels their unique characteristics. Gelatin is non-toxic and non-irritant to normal skin and eyes and forms stable, elastic gels.

Lime processed gelatins are slightly more stable than acid processed gelatins, particularly in relation to pH values. The shaped gel shower products may have a pH of between 5 and 7. If for any reason the pH is low i.e. less than 5, then the rigidity of the gel decreases. This decrease is significantly sharper with an acid processed gelatin than with a lime processed one.

Although any gelatin may be used in the product according to the invention, it is advantageous to use gelatin that has been manufactured by alkali-treatment of collagen, as gelatins produced by alkali-treatments are in general more pure than gelatins produced by acid treatment of collagen and therefore give rise to stronger more stable gels. It is preferred to use a gelatin having a Bloom strength of in the region of 200 g. Gelatins having a Bloom strength in the range 170 g to 230 g, for example 180 g to 220 g, for example 190 g to 210 g, preferably 200 g may give advantageous results.

The term Bloom strength is used herein in relation to gelatin to indicate the gel strength that is the force (expressed in grammes) required to depress the surface of six ⅔% w/w gel, matured at 10° C. for 16 to 18 hours, a distance of 4 mm using a flat-bottomed plunger 12.7 mm in diameter.

When the gelatin is mixed with heat and water it dissolves and, on cooling, the mixture sets as a gel, consisting of continuous aqueous phase and gelatin phases. It is believed that, on setting, a rearrangement of the individual gelatin molecules occurs, giving chain segments that are helical in configuration providing strong but elastic structure. Other substances, for example surfactant molecules, that may be present in the gelatin solution before setting become trapped in the gel structure.

Aptly, an embodiment of the invention provides a formulation, product and/or process wherein the gelatin has a bloom strength of less than or equal to 230 g, for example less than or equal 220 g, for example less than or equal or 210 g, for example less than or equal to 200 g. An embodiment also provides a formulation, product and/or process wherein the gelatin has a bloom strength of at least than 170 g, for example at least 180 g, for example at least 190 g, for example at least 200 g. In particular, an embodiment of the invention provides a formulation, product and/or process comprising gelatin having a bloom strength of from 170 g to 230 g, for example 180 g to 220 g, for example 190 g to 210 g, for example approximately 200 g, for example 200 g. More particularly, gelatin has a bloom strength of 200 g.

Aptly, an embodiment of the invention provides a formulation, product and/or process wherein the gelatin is present in a quantity of less than or equal to 10% by weight, for example less than or equal to 9% by weight, for example less than or equal to 8% by weight, for example less than or equal to 7% by weight, for example less than or equal to 6% by weight. An embodiment also provides a formulation, product and/or process comprising gelatin in a quantity of at least 5% by weight, for example at least 6% by weight, for example at least 7% by weight, for example at least 8% by weight. In particular, an embodiment of the invention provides a formulation, product and/or process comprising gelatin in a quantity of 5 to 9% by weight, for example 6 to 9% by weight, for example 6 to 8% by weight, for example 6.5 to 7.5% by weight, for example approximately 7% by weight, for example 7% by weight. More particularly, gelatin is in a quantity of 7% by weight.

For the present invention, it is preferred that the gelatin content and/or bloom strength is chosen so that the product dissolves in a controlled and gradual manner when it comes into contact with warm water in use.

The amount of water present in the formulation must be sufficient to allow the gelatin to hydrate and start to form into the protein structure that will form the basis of the semi-solid gel structure of the product. Generally water is in a quantity of at least 15% by weight. The actual amount of water to be used should be chosen having regard to the need to form a stable gel having the desired dissolution characteristics in water and with regard to the other ingredients of the formulation. For shower gels, it is preferred that the product contain from 1 to 4 parts water per part gelatin.

It will be appreciated that water may be added to or be present in the formulation in the form of one or more solution(s) containing other ingredients. For example, gelatin may be added to an aloe vera extract. The aloe vera extract contains sufficient water to allow the gelatin to hydrate. In certain embodiments, the aloe vera extract is in gel form and comprises approximately 99.5% water by weight. In one embodiment, the water is comprised in a solution with surfactant as described herein.

The formulation, product and/or process of the invention comprises surfactant. Surfactants may be described as primary surfactants or secondary surfactants. Primary surfactants may be used without other surfactants for their foam generating and/or cleansing properties. Primary surfactants are often anionic surfactants. A secondary surfactant can be described as any surfactant that is used in conjunction with a primary surfactant to enhance one or more property of the primary surfactant, for example foaming characteristics, viscosity responses, or to improve the overall mildness of a formulation. Secondary surfactants can also be described as foam boosters, emulsifiers and/or stabilisers.

The invention may comprise primary surfactant and optionally secondary surfactant.

A surfactant of the invention may be anionic, amphoteric or nonionic.

Examples of anionic surfactants include sulfate, sulfonate, and phosphate esters, docusates and carboxylates. A surfactant may be selected from ammonium lauryl sulfate, sodium lauryl sulfate, sodium laureth sulfate and sodium myreth sulfate. A surfactant may be selected from dioctyl sodium sulfosuccinate, perfluorooctanesulfonate (PFOS), perfluorobutanesulfonate and linear alkylbenzene sulfonates (LABs). A surfactant may be selected from sodium stearate, sodium lauroyl sarcosinate and carboxylate-based fluorosurfactants such as perfluorononanoate, perfluorooctanoate (PFOA or PFO).

Other examples of anionic surfactants include isethionates (also known as 2-hydroxyethanesulfonates). Isethionate surfactants may be prepared from isethionic acid or by the reaction of a fatty acid chloride with sodium or ammonium isethionate and can be prepared from coconut oil. Isethionates are known to be particularly mild surfactants i.e. mild to skin and an effective cleaning agent, producing a creamy lather. Examples of isethionate surfactants include lauroyl methyl sodium isethionate, sodium cocoyl isethionate, ammonium cocoyl isethionate, sodium hydrogenated cocoyl methyl isethionate, sodium isethionate, sodium lauroyl isethionate, sodium methyl isethionate, sodium myristoyl isethionate, sodium oleoyl isethionate, sodium oleyl methyl isethionate, sodium palm kerneloyl isethionate and sodium stearoyl methyl isethionate.

Examples of amphoteric surfactants include phospholipids phosphatidylserine, phosphatidylethanolamine, phosphatidylcholine, and sphingomyelins. Another example of an amphoteric surfactant is lauryl betaine.

Examples of non-ionic surfactant include fatty alcohols, cetyl alcohol, stearyl alcohol and cetostearyl alcohol (consisting predominantly of cetyl and stearyl alcohols), and oleyl alcohol. A surfactant may be selected from polyoxyethylene glycol alkyl ethers (Brij): $CH_3-(CH_2)_{10-16}-(O-C_2H_4)_{1-25}-OH$, octaethylene glycol monododecyl ether, pentaethylene glycol monododecyl ether, polyoxypropylene glycol alkyl ethers: $CH_3-(CH_2)_{10-16}-(O-C_3H_6)_{1-25}-OH$, glucoside alkyl ethers: $CH_3-(CH_2)_{10-16}-(O-Glucoside)_{1-3}-OH$, decyl glucoside, lauryl glucoside, octyl glucoside, polyoxyethylene glycol octylphenol ethers: $C_8H_{17}-(C_6H_4)-(O-C_2H_4)_{1-25}-OH$, triton X-100, polyoxyethylene glycol alkylphenol ethers: $C_9H_{19}-(C_6H_4)-(O-C_2H_4)_{1-25}-OH$, nonoxynol-9, glycerol alkyl esters (for example glyceryl laurate), polyoxyethylene glycol sorbitan alkyl esters (for example polysorbate), sorbitan alkyl esters, cocamide MEA, cocamide DEA, dodecyldimethylamine oxide, block copolymers of polyethylene glycol and polypropylene glycol: poloxamers, and polyethoxylated tallow amine (POEA). Another example of a non-ionic surfactant is cocoglucoside.

Aptly, an embodiment of the invention provides a formulation, product and/or process wherein the surfactant, for example a primary surfactant, is selected from an isethionate surfactant.

Aptly, in an embodiment of the invention, the surfactant is selected from lauroyl methyl sodium isethionate, sodium cocoyl isethionate, ammonium cocoyl isethionate, sodium hydrogenated cocoyl methyl isethionate, sodium isethionate, sodium lauroyl isethionate, sodium methyl isethionate, sodium myristoyl isethionate, sodium oleoyl isethionate, sodium oleyl methyl isethionate, sodium palm kerneloyl isethionate and sodium stearoyl methyl isethionate.

Aptly, in an embodiment of the invention, the surfactant is selected from lauroyl methyl sodium isethionate, sodium cocoyl isethionate, ammonium cocoyl isethionate, sodium isethionate, sodium lauroyl isethionate and sodium methyl isethionate.

Aptly, in an embodiment of the invention, the surfactant is lauroyl methyl sodium isethionate.

Aptly, in an embodiment of the invention, the surfactant, for example lauroyl methyl sodium isethionate, is present in a quantity of less than or equal to 18% by weight, for example less than or equal to 16% by weight, for example less than or equal to 13% by weight, for example less than or equal to 10% by weight. In an embodiment, the surfactant, for example lauroyl methyl sodium isethionate is present in a quantity of at least 5% by weight, for example at least 7% by weight, for example at least 8% by weight, for example at least 10% by weight. In particular, in an embodiment of the invention, the surfactant, for example lauroyl methyl sodium isethionate is present in a quantity of from 5 to 18% by weight, for example 7 to 16% by weight, for example 8 to 13% by weight, for example from 8 to 10% by weight, for example from 9 to 10% by weight, for example approximately 9.6% by weight, for example 9.6% by weight.

Aptly, in an embodiment of the invention, the surfactant, for example lauroyl methyl sodium isethionate, is present in or added to the formulation and/or product of the invention as a surfactant solution wherein the solution is present in a quantity of from 15 to 50% by weight, for example 20 to 50% by weight, for example from 20 to 45% by weight, for example 25 to 40% by weight, for example 30 to 40% by weight, for example 25 to 35% by weight, for example approximately 30% by weight. The surfactant solution may comprise surfactant, for example lauroyl methyl sodium isethionate, in the range of 20 to 50% by weight of solution, for example 25 to 45% weight of solution, for example 30 to 35% by weight of solution, for example approximately 32% by weight of solution. The surfactant solution may comprise water in the range 50 to 85% by weight of solution, for example 80 to 65% by weight of solution, for example 60 to 70% by weight of solution, for example 65 to 70% by weight of solution, for example approximately 68% by weight of solution, for example 68% by weight of solution.

Lauroyl methyl sodium isethionate is available commercially, for example from Innospec Performance Chemicals.

Lauroyl methyl sodium isethionate is available commercially as a surfactant solution, for example approximately 32% lauroyl methyl sodium isethionate/68% water by weight of solution (for example available as Iselux LQ-CLR-SB)

Lauroyl methyl sodium isethionate is available commercially as a surfactant blend, for example a blend comprising lauroyl methyl sodium isethionate, sodium lauroamphoacetate and cocamide MIPA (for example available as Iselux SLC).

Aptly, in an embodiment of the invention, the surfactant is selected from disodium laureth sulfosuccinate, sodium $C_{14-16}$ olefin sulfonate, sodium laureth sulfate, and lauramide DEA.

Aptly the surfactant is sodium laureth sulfate (sodium laureth ether sulfate SLES).

Aptly the surfactant, for example sodium laureth sulfate, is present as a surfactant solution at a quantity of from 40 to 60% by weight, for example from 45 to 55% by weight, for example 50% by weight. The surfactant solution may comprise surfactant in the range of 25 to 35% by weight, for example approximately 30% by weight. The surfactant solution may comprise water in the range 65 to 75% by weight, for example approximately 70% by weight.

Aptly the surfactant, for example sodium laureth sulfate, is present as a surfactant solution at a quantity of from 15 to 25% by weight, for example from 18 to 22% by weight, for example approximately 21.5% by weight. The surfactant solution may comprise surfactant in the range of 65 to 75% by weight, for example approximately 70% by weight. The surfactant solution may comprise water in the range 25 to 35% by weight, for example approximately 30% by weight.

Aptly the surfactant, for example sodium laureth sulfate, is present at a quantity of from 12 to 18% by weight, for example from 13.5 to 16.5% by weight, for example approximately 15% by weight.

In an embodiment, the formulation, product and/or process of the invention comprises a secondary surfactant. The secondary surfactant may act as an emulsifier, foam booster, stabiliser and/or viscosity enhancer.

Aptly, in an embodiment of the invention, the invention comprises sodium lauroamphoacetate. Sodium lauroamphoacetate is an amphoteric surfactant used as a mild, sulfate free primary surfactant.

Aptly, in an embodiment of the invention, the invention comprises cocamide MIPA. Cocamide MIPA is a mixture of isopropanolamides of Coconut Acid and is used as a mild secondary surfactant, foam booster and stabiliser.

The invention may comprise a secondary surfactant. The secondary surfactant may act as an emulsifier. Examples include cocamide DEA and PPG-2 hydroxyethyl cocamide.

Aptly, in an embodiment, the invention comprises an emulsifier. The emulsifier may be selected from cocamide DEA and PPG-2 hydroxyethyl cocamide. Aptly, in an embodiment, the invention comprises PPG-2 hydroxyethyl cocamide.

PPG-2 hydroxyethyl cocamide is a mild surfactant derived from coconut oil. It is often used as an emulsifier to allow oils and fragrances to combine with aqueous materials.

Cocamide DEA (cocamide diethanolamide) is a diethanolamide made by reacting the mixture of fatty acids from coconut oil with diethanolamine. It is a viscous liquid and is used as a foaming agent in bath products and in cosmetics as an emulsifying agent. The chemical formula of individual components is $CH_3(CH_2)_nC(=O)N(CH_2CH_2OH)_2$ where n typically ranges from 8 to 18.

Aptly, in an embodiment, an emulsifier, for example PPG-2 hydroxyethyl cocamide, is present in a quantity of less than or equal to 10% by weight, for example less than or equal to 7.5% by weight, for example less than or equal to 6% by weight, for example less than or equal to 5% by weight. In an embodiment, an emulsifier, for example PPG-2 hydroxyethyl cocamide, is present in a quantity of at least 2.5% by weight, for example at least 3% by weight, for example at least 5% by weight. In particular, an emulsifier, for example PPG-2 hydroxyethyl cocamide, is present in a quantity of from 2.5% to 10% by weight, for example from 2.5% to 7.5% by weight, for example 3 to 6% by weight, for example approximately 5% by weight, for example 5% by weight.

The invention may comprise a secondary surfactant. The secondary surfactant may influence (for example increase) bubble size of a lather produced by a product of the invention. The quality of a lather is depend on bubble size with users often having a preference for large open bubbles over small close-knit bubbles. Examples include coco glucoside, sodium laureth sulfate and ammonium laureth sulfate.

Aptly, in an embodiment, the invention comprises coco glucoside.

Aptly, in an embodiment, the invention comprises coco glucoside present in a quantity of less than or equal to 20% by weight, for example less than or equal to 15% by weight, for example less than or equal to 12% by weight, for example less than or equal to 10% by weight. In an embodiment, the invention comprises coco glucoside present in a quantity of at least 5% by weight, for example at least 8% by weight, for example at least 10% by weight. In particular, coco glucoside may be present in a quantity of 5 to 20% by weight, for example 5 to 15% by weight, for example 8 to 12% by weight, for example approximately 10% by weight, for example 10% by weight.

The invention may comprises a secondary surfactant. The secondary surfactant may act as a foam booster and/or viscosity enhancer. Examples include coco betaine, lauryl betaine and cocoamidopropyl betaine.

Aptly, in an embodiment, the invention comprises lauryl betaine.

Aptly, in an embodiment, the invention comprises a foam booster and/or viscosity enhancer, for example lauryl betaine, in a quantity of less than or equal to 10% by weight, for example less than or equal to 8% by weight, for example less than or equal to 6% by weight, for example less than or equal to 5% by weight. In an embodiment, a foam booster and/or viscosity enhancer, for example lauryl betaine, in a quantity of at least 2% by weight, for example at least 4% by weight, for example at least 5% by weight. In particular, an embodiment of the invention comprises a foam booster and/or viscosity enhancer, for example lauryl betaine, in a quantity of 2 to 10% by weight, for example 2 to 8% by weight, for example 4 to 6% by weight, for example approximately 5% by weight, for example 5% by weight.

The presence of a humectant in a product of the invention may be desirable to hinder the loss of moisture. It is believed that the presence of a humectant may contribute towards the pleasing appearance and tactility of products of the invention. The type and quantity of the humectant may also have particular advantages.

Aptly, an embodiment of the invention provides a formulation, product and/or process comprising a humectant. Aptly, the humectant is selected from polyhydric alcohols, for example glycerine, propylene glycol and PEG-7 glyceryl cocoate. Aptly an embodiment of the invention provides a formulation, product and/or process comprising glycerine.

Aptly, an embodiment of the invention provides a formulation, product and/or process wherein the humectant is present in a quantity of less than or equal to 30% by weight, for example less than or equal to 25% e.g. less than or equal to 22% by weight, for example less than or equal to 20% by weight. An embodiment also provides a formulation, product and/or process comprising humectant in a quantity of at least 5% by weight, for example at least 10% by weight, for example at least 20% by weight. In particular, an embodiment of the invention provides a formulation, product and/or process comprising humectant in a quantity of 5 to 30% by weight, for example from 10 to 30% weight, for example from 15 to 30% by weight, for example from 20 to 30% weight, for example 18 to 23% weight. Particularly, a humectant is present in a quantity of 20 to 22% by weight, for example 21%. More particularly, a humectant is glycerine and is present at a quantity of from 10 to 30% by weight, for example from 15 to 30% weight, for example 20 to 30% by weight, for example 20.5 to 21.5% by weight, for example 21% by weight.

Aptly, an embodiment of the invention provides a formulation, product and/or process comprising humectant wherein the humectant is glycerine and present in a quantity of 20.5 to 21.51% by weight, for example 21% by weight.

The presence of a preservative in a product of the invention may be desirable to enhance the shelf life of the product. An adequate amount of preservative can prevent attack by moulds and bacteria. Bacteria and fungal attack can produce opacity in products that are clear, separation in emulsions and pearlescent products and can cause changes in both perfume and colour systems. Fermentation can also occur causing a complete breakdown of the product potentially rendering the product dangerous.

The preservative must be selected that is suitable for the product and in accordance with the legislative requirements in the country of sale.

Aptly, a formulation, product and/or process of the invention may also comprise a preservative. A preservative may comprise parabens. Aptly, a preservative system may selected from:
Phenonip® (phenoxyethanol, methylparaben, ethylparaben, butylparaben, propylparaben, isobutylparaben) (for example available from Clariant);
Phenochem (phenoxyethanol, methylparaben, ethylparaben, butylparaben, propylparaben);
Benzyl alcohol, salicyclic acid, glycerine and sorbic acid (for example available Adina Cosmetic Ingredients);
Methylchloroisothiazolinone and methylisothiazolinone (for example available from Clariant); and
Benzyl alcohol and dehydroacetic acid (for example available from Adina Cosmetic Ingredients).

These preservatives are readily available commercially.

Aptly, a formulation, product and/or process of the invention may also comprise benzyl alcohol and dehydroacetic acid (for example Geogard 221).

Aptly, an embodiment of the invention provides a formulation, product and/or process wherein the preservative is present at a quantity of less than or equal to 2% by weight, for example less than or equal to 1.5% by weight, for example less than or equal to 1% by weight. An embodiment also provides a formulation, product and/or process comprising preservative in a quantity of at least 0.1% by weight, for example at least 0.2% by weight, for example at least 0.5% by weight, for example at least 0.7% by weight, for example at least 1% by weight. In particular, an embodiment of the invention provides a formulation, product and/or process comprising preservative in a quantity of from 0.1 to 2% by weight, for example 0.5 to 2% by weight, for example 0.5 to 1.5% by weight, for example 0.7 to 1.5% by weight, for example 0.8 to 1.2% by weight. More particularly, preservative is present at a quantity of 0.9 to 1.1% by weight. More particularly, preservative is present at a quantity of 0.95 to 1.05% by weight. More particularly, preservative is present at a quantity of 1% by weight. Aptly the preservative, for example benzyl alcohol and dehydroacetic acid is present at a quantity of 1%.

Aptly, a formulation, product and/or process of the invention may also comprise fragrance.

Aptly, an embodiment of the invention provides a formulation, product and/or process wherein the fragrance is present at a quantity of from 0.05 to 2% by weight. More particularly, a fragrance is present at a quantity of 0.05 to 1.5% by weight. More particularly, a fragrance is present at a quantity of 0.05 to 1% by weight. More particularly, a fragrance is present at a quantity of 0.25 to 1.25% by weight. More particularly, a fragrance is present at a quantity of 0.25 to 0.75% by weight. More particularly, a fragrance is present at a quantity of 0.4 to 0.6% by weight. More particularly, a fragrance is present at a quantity of 0.5% by weight.

Aptly, a formulation, product and/or process of the invention may also comprise a colour in particular cosmetic synthetic grade or vegetable colourings.

Aptly, a formulation, product and/or process of the invention may also be pH adjusted. For example citric acid may be used. Aptly, the pH of the formulation and/or product is between pH 5 and 7, for example pH 5.5.

The formulation, product and/or process of the invention may also include one or more further ingredients selected from:
Natural extracts, for example aloe vera extract;
oils, for example avocado oil;
conditioning agents,
pigments, for example mica pigments;

pearling agents, for example glycol distearate;
UV stabilisers, for example benzophenone-1; and
emulsifers, for example cetyl stearyl alcohol.

In an aspect of the present invention there is provided a process for the preparation of a formulation of the invention comprising the steps of:
  i) mixing gelatin with water;
  ii) adding surfactant to the gelatin mixture and optionally heating, for example to approximately 70° C.;
  iii) optionally, adding any other ingredients to the gelatin mixture;
  iv) if required, adjusting the pH of the gelatin mixture to between pH 5 to pH 7; and optionally,
  v) forming the solution/mixture into the desired shape(s); and/or
  vi) forming a gel, for example by cooling the mixture.

Aptly, the gelatin is dissolved in water in a quantity of from 5 to 10% by weight based on the total weight of the formulation. Aptly, the gelatin has a bloom strength of 170 g to 230 g.

The shaped gel product of the invention may be prepared by a process comprising steps i), ii), iii), iv), v) and vi) as described above.

In step i), the gelatin is combined with an amount of water sufficient to form a gel. The water may be present as a solution, for example as aloe vera extract.

The surfactant and/or other ingredients may be added to mixture before or after a heating step. Aptly, the surfactant is added before the heating step (i.e. after the gelatin has dissolved in water). Adding surfactant after dissolving the gelatin assists with cooling of the mixture.

The mixture is cooled to a temperature of between 40° C. and 50° C., for example 45° C. to 50° C. Other ingredients such as fragrance may be added after cooling.

Once a gel has formed and the product has been shaped, the product may then be placed or rapped in suitable packaging. Preferably the packaging is airtight. If desired, the mixture may be placed in a mould that is suitable for inclusion in the packaging in which the product is to be sold. In that case, after the gel has set, the mould containing the shaped product is preferably packed in a suitable container. It has been found that the use of such a mould, particularly one which encloses the product, is advantageous in that it reduces the occurrence of moisture loss from the product.

In accordance with the invention, the gel may be allowed to set in any desired shape, for example resembling the shape of an animal or another object that might be regarded as appealing by consumers, for example by children.

In accordance with the invention, the gel may be poured, whilst in a liquid form, onto or into a substrate and allowed to set as a coating or within the substrate to form a multi-component shower product. In certain embodiments, the substrate may be a porous structure e.g. a sponge and the gel may be poured into multiple pores of the substrate and allowed to set within the pores. In certain embodiments, the substrate may comprise a netting or mesh element and the gel, when in a liquid form, may be poured into pores of the netting or mesh and allowed to set. Once set, the gel is in a shaped form as dictated by the dimensions of the pores of the substrate.

Aptly, the following definitions are used herein.

It should be noted that where values are provided as '% by weight' or '% wt', these values are based on the total weight of the formulation, unless otherwise stated. These values are calculated from the actual weights of each ingredient of the formulation as they are added to the formulation and the total weight of the formulation.

The term "shower product" means a toiletry product intended to be applied directly to the body by hand or via a cleaning implement, in the presence of water. In certain embodiments, the shower product comprises a shaped gel product as described herein and a further component. Aptly, the further component is a substrate for the shaped gel product. Aptly, the substrate may be a porous substrate e.g. a sponge. In certain embodiments, the substrate comprises a netting or mesh component. The substrate may accommodate and/or be coated by a formulation as a shaped gel as described herein.

The phrases "shaped gel" and "shaped gel form" mean a semi-solid gel form, i.e. a gel form that is sufficiently solid to maintain its structural integrity over an extended period of use and that can be used multiple times whilst being sufficiently pliant to conform to the contours of the body on application. The gel form is self-supporting and pliable. In certain embodiments the shape and/or dimensions of the shaped gel form are dictated or constrained by the dimensions of pores or apertures of a substrate as described herein. Such substrates include for example sponges, meshes and/or nettings or the like. In certain embodiments, the shaped gel form is an irregular shape. In certain embodiments, the shaped gel form may be non-contiguous.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

DETAILED DESCRIPTION OF EMBODIMENTS OF THE INVENTION

Embodiments of the present invention will now be described herein, by way of example only.

Examples 1 and 2

TABLE 1

| Material Quantity | | INCI | Example 1 Quantity % | Example 2 Quantity % |
|---|---|---|---|---|
| Phase A | | | | |
| 1 | DI Water | Aqua | 20.50% | 20.50% |
| 2 | Gelatin 200 bloom | Gelatin | 7.00% | 7.00% |
| Phase B | | | | |
| 3 | Glycerin | Glycerin | 21.00% | 21.00% |
| 4 | Lauryl Betaine | Lauryl Betaine | 5.00% | 5.00% |
| 5 | Iselux LQ-CLR-SB | Lauroyl Methyl Sodium Isethionate | 30.00% | N/A |
| 5a | Iselux SLC | Sodium Lauroyl Methyl Isethionate (and) Sodium Lauroamphoacetate (and) | N/A | 30.00% |
| 6 | Plantacare 818 | Coco Glucoside | 10.00% | 10.00% |
| Phase C | | | | |
| 7 | Promidium CO-LQ | PPG-2 Hydroxyethyl Cocamide | 5.00% | 5.00% |
| 8 | Fragrance: | Parfum | 0.50% | 0.50% |
| Phase D | | | | |
| 9 | Geogard 221 | Dehydroacetic acid and Benzyl Alcohol | 1.00% | 1.00% |
| 10 | Colour | | qs | qs |
| 11 | Citric Acid | Citric Acid | qs pH 5.50 | qs pH 5.50 |

A. Cold water (% by weight as shown in table 1) was placed in a mixing receptacle and gelatin powder (% by weight as shown in table 1; lime processed; Bloom strength 200 g) was added and left for 30 minutes to swell.

B. Ingredients 3 to 6 were added to gelatin mixture and heated to 70° C.

C. Ingredient 8 was mixed well into ingredient 7 and then added slowly to gelatin mixture between 45° C. and 50° C.

D. Ingredients 9 and 10 were then added and the pH adjusted using ingredient 11 as required.

E. The mixture was then placed in moulds and allowed to cool. After cooling, it was found that the mixture had set to form a shaped article which could be removed from the mould.

In an alternative embodiment, the method comprises mixing gelatin powder (% by weight as shown in table 1; lime processed; Bloom strength 200 g) with any one or more of Ingredients 1 or 3 to 6. The mixture is optionally left for 30 minutes before the remaining ingredients are added and the mixture is then heated to 70° C. The mixture is then allowed to cool before being reheated to approx. 50° C. The mixture is stirred using a mechanical stirrer for approx. 10 minutes and then the pH was adjusted using Ingredient 11. The mixture is then placed in moulds and allowed to cool. After cooling, the mixture sets to form a shaped article which could be formed from the mould.

Example 3

| | Material | INCI | Quantity % |
|---|---|---|---|
| Phase A | | | |
| 1 | Aloe vera (aqueous solution) | Aloe vera | 17.90% |
| 2 | Gelatin 200 bloom | Gelatin | 7.00% |
| Phase B | | | |
| 3 | Lauryl Betaine | Lauryl Betaine | 5.00% |
| 4 | Iselux LQ-CLR-SB | Lauroyl Methyl Sodium Isethionate | 30.00% |
| 5 | Plantacare 818 | Coco Glucoside | 10.00% |
| 6 | Glycol Distearate | Glycol Distearate | 2.00% |
| Phase C | | | |
| 7 | Glycerin | Glycerin | 21.00% |
| 8 | PQ-10 | Polyquaternium-10 | 0.50% |
| Phase D | | | |
| 9 | Promidium CO-LQ | PPG-2 Hydroxyethyl Cocamide | 5.00% |
| 10 | Organic Avocado oil | *Persea gratissima* (Avocado) oil | 0.10% |
| 11 | Fragrance: | Parfum | 0.50% |
| Phase E | | | |
| 12 | Geogard 221 | Dehydroacetic acid and Benzyl Alcohol | 1.00% |
| 13 | Colour | | qs |
| 14 | Citric Acid | Citric Acid | qs pH 5.50 |

A. Aloe vera extract was added to gelatin which was allowed to swell for 30 minutes.

B. Ingredients 3 to 6 were then added.

C. Ingredient 8 was mixed with ingredient 7 and then added to the gelatin mixture which was heated to 70° C.

D. Ingredients 10 and 11 were mixed with ingredient 9 and then added to the gelatin mixture at a temperature of 50° C. or less.

E. Ingredient 12 was mixed with ingredient 13 and added to the gelatin mixture. The pH was adjusted with ingredient 14 as required.

F. The mixture was then placed in moulds and allowed to cool. After cooling, it was found that the mixture had set to form a shaped article which could be removed from the mould.

The invention claimed is:

1. A formulation, comprising:
water, gelatin at a quantity of 5 to 9% by weight, sodium lauroyl methyl isethionate at a quantity of 9 to 10% by weight, coco glucoside at a quantity of 8 to 12% by weight, lauryl betaine at a quantity of 4 to 6% by weight, PPG-2 hydroxyethyl cocamide at a quantity 3 to 6% by weight, glycerine at a quantity of 20.5 to 21.5% by weight, preservative comprising dehydroacetic acid and benzyl alcohol at a quantity of 0.9 to 1.1% by weight, fragrance at a quantity of 0.25 to 1.25% by weight, and colour.

2. The formulation of claim 1, comprising gelatin at a quantity of 7% by weight, sodium lauroyl methyl isethionate at a quantity of 9.6% by weight, coco glucoside at a quantity of 10% by weight, lauryl betaine at a quantity of 5% by weight, PPG-2 hydroxyethyl cocamide at a quantity 5% by weight, glycerine at a quantity of 21% by weight, preservative comprising dehydroacetic acid and benzyl alcohol at a quantity of 1% by weight, and fragrance at a quantity of 1% by weight.

3. A shower product comprising the formulation of claim 1, in a shaped gel form.

4. The product according to claim 3, further encased in an airtight package.

5. The product according to claim 3, further comprising a porous component comprising pores in which the shaped gel form is located.

6. A method for the preparation of the shower product of claim 3, comprising:
   i) mixing gelatin with water to form a gelatin mixture;
   ii) adding the sodium lauroyl methyl isethionate to the gelatin mixture and optionally heating to 70° C.;
   iii) adding the coco glucoside, lauryl betaine, PPG-2 hydroxyethyl cocamide, glycerine, preservative comprising dehydroacetic acid and benzyl alcohol, fragrance, and colour to the gelatin mixture;
   iv) adjusting the pH of the gelatin mixture to pH 5 to pH 7;
   v) forming the mixture into a shape; and/or
   vi) forming a gel by cooling the mixture.

7. The formulation of claim 1, wherein the gelatin has a bloom strength of 170 to 230.

8. The formulation if claim 7, wherein the water is present in a quantity of at least 15% by weight.

9. The product of claim 3, wherein the gelatin has a bloom strength of 170 to 230.

10. The product of claim 9, wherein the water is present in a quantity of at least 15% by weight.

11. The method of claim 6, wherein the gelatin has a bloom strength of 170 to 230.

12. The method of claim 11, wherein the water is present in a quantity of at least 15% by weight.

* * * * *